United States Patent
Guan et al.

(10) Patent No.: US 10,619,264 B2
(45) Date of Patent: Apr. 14, 2020

(54) METHOD OF PREPARING COATING OF BIOMEDICAL MAGNESIUM ALLOYS AND MAGNESIUM OR MAGNESIUM ALLOY COMPRISING THE COATING

(71) Applicant: Zhengzhou University, Zhengzhou (CN)

(72) Inventors: Shaokang Guan, Zhengzhou (CN); Di Mei, Zhengzhou (CN); Yashan Feng, Zhengzhou (CN); Shijie Zhu, Zhengzhou (CN); Jun Wang, Zhengzhou (CN); Liguo Wang, Zhengzhou (CN); Yanhua Wang, Zhengzhou (CN)

(73) Assignee: ZHENGZHOU UNIVERSITY, Zhengzhou (CN)

( * ) Notice: Subject to any disclaimer, the term of this patent is extended or adjusted under 35 U.S.C. 154(b) by 14 days.

(21) Appl. No.: 16/022,671

(22) Filed: Jun. 28, 2018

(65) Prior Publication Data
US 2018/0305835 A1 Oct. 25, 2018

Related U.S. Application Data

(63) Continuation-in-part of application No. PCT/CN2016/099674, filed on Sep. 22, 2016.

(30) Foreign Application Priority Data

Jan. 5, 2016 (CN) .......................... 2016 1 0001969

(51) Int. Cl.
*C25D 3/56* (2006.01)
*C25D 11/36* (2006.01)
(Continued)

(52) U.S. Cl.
CPC .............. *C25D 9/12* (2013.01); *A61L 27/047* (2013.01); *A61L 27/32* (2013.01); *A61L 27/58* (2013.01);
(Continued)

(58) Field of Classification Search
CPC .. B25B 15/00; C25D 9/12; C25D 3/56; C25D 3/565; C25D 11/36
(Continued)

(56) References Cited

PUBLICATIONS

Phuong et al., "Zinc Phosphate Conversion Coatings on Magnesium Alloys: A Review," Met. Mater. Int. (2013), vol. 19, No. 2, pp. 273-281. (Year: 2013).*
(Continued)

*Primary Examiner* — Edna Wong
(74) *Attorney, Agent, or Firm* — Matthias Scholl P.C.; Matthias Scholl

(57) ABSTRACT

A method including: employing pure magnesium or a magnesium alloy as a substrate material, and sanding and cleaning the substrate material; preparing an electrolyte including 0.8-8 mmol/L of $Zn^{2+}$, 30-50 mmol/L of $Ca^+$, 15-35 mmol/L of $H_2PO_4^-$, 0-0.5 mol/L of $NaNO_3$, and 0-0.05 mmol/L of a magnesium ion complexing agent; employing the substrate material as a cathode, a graphite flake as an anode, heating the electrolyte to a temperature of between 60 and 90° C., and synchronously immersing the cathode and the anode into the electrolyte; and implementing an electrochemical deposition method in the electrolyte for between 20 and 60 min.

7 Claims, 5 Drawing Sheets

| Element | Weight percentage (%) | Atomic percentage (%) |
|---|---|---|
| C | 7.47 | 15.48 |
| O | 33.57 | 52.26 |
| P | 17.66 | 14.20 |
| Ca | 9.65 | 6.00 |
| Zn | 31.65 | 12.06 |

(51) Int. Cl.
　　　*C25D 9/12*　　　(2006.01)
　　　*A61L 27/04*　　　(2006.01)
　　　*C25D 5/42*　　　(2006.01)
　　　*C25D 5/18*　　　(2006.01)
　　　*C25D 3/22*　　　(2006.01)
　　　*A61L 27/32*　　　(2006.01)
　　　*A61L 27/58*　　　(2006.01)

(52) U.S. Cl.
　　　CPC .............. *C25D 3/22* (2013.01); *C25D 5/18* (2013.01); *C25D 5/42* (2013.01); *A61L 2420/02* (2013.01); *A61L 2430/02* (2013.01)

(58) Field of Classification Search
　　　USPC .................................. 428/544; 205/244, 238
　　　See application file for complete search history.

(56) References Cited

PUBLICATIONS

Zeng et al., Characterization of Calcium-Modified Zinc Phosphate Conversion Coatings and Their Influences on Corrosion Resistance of AZ31 Alloy, Surface & Coatings Technology (2011), vol. 205, pp. 3347-3355. (Year: 2011).*

Zeng et al., "Corrosion Resistance of Calcium-Modified Zinc Phosphate Conversion Coatings on Magnesium-Aluminium Alloys," Corrosion Science (2014), vol. 88, pp. 452-459. (Year: 2014).*

* cited by examiner

| Element | Weight percentage (%) | Atomic percentage (%) |
|---------|----------------------|----------------------|
| C | 7.47 | 15.48 |
| O | 33.57 | 52.26 |
| P | 17.66 | 14.20 |
| Ca | 9.65 | 6.00 |
| Zn | 31.65 | 12.06 |

FIG. 2B

METHOD OF PREPARING COATING OF BIOMEDICAL MAGNESIUM ALLOYS AND MAGNESIUM OR MAGNESIUM ALLOY COMPRISING THE COATING

CROSS-REFERENCE TO RELATED APPLICATIONS

This application is a continuation-in-part of International Patent Application No. PCT/CN2016/099674 with an international filing date of Sep. 22, 2016, designating the United States, now pending, and further claims foreign priority benefits to Chinese Patent Application No. 201610001969.X filed Jan. 5, 2016. The contents of all of the aforementioned applications, including any intervening amendments thereto, are incorporated herein by reference. Inquiries from the public to applicants or assignees concerning this document or the related applications should be directed to: Matthias Scholl P C., Attn.: Dr. Matthias Scholl Esq., 245 First Street, 18th Floor, Cambridge, Mass. 02142.

BACKGROUND

The disclosure relates to the field of surface treatment of biomedical magnesium alloys, and more particularly to a method of preparing a coating of biomedical magnesium alloys and a magnesium or magnesium alloy comprising the coating.

Because of its biodegradability and elastic modulus that is similar to human bone, magnesium alloy is a promising biodegradable medical bone implant material. However, most magnesium and magnesium alloys corrode too fast in human physiological environment.

SUMMARY

The disclosure provides a method of preparing a coating of biomedical magnesium alloys that can improve the corrosion resistance and biocompatibility of the alloys.

Disclosed is a method of preparing a coating of biomedical magnesium alloys, the method comprising:
1) employing pure magnesium or a magnesium alloy as a substrate material, and sanding and cleaning the substrate material;
2) preparing an electrolyte comprising 0.8-8 mmol/L of $Zn^{2+}$, 30-50 mmol/L of $Ca^{2+}$, 15-35 mmol/L of $H_2PO_4^-$, 0-0.5 mol/L of $NaNO_3$, and 0-0.05 mmol/L of a magnesium ion complexing agent;
3) employing the substrate material in 1) as a cathode, a graphite flake as an anode, heating the electrolyte to a temperature of between 60 and 90° C., and synchronously immersing the cathode and the anode into the electrolyte in 2), a distance between the cathode and the anode being between 3 and 5 cm; and
4) implementing an electrochemical deposition method in the electrolyte for between 20 and 60 min.

The $Zn^{2+}$ can be selected from $Zn(NO_3)_2 \cdot 6H_2O$, $Zn(H_2PO_4)_2 \cdot 2H_2O$, and a mixture thereof.

The $Ca^{2+}$ can be selected from $Ca(NO_3)_2$, $Ca(NO_3)_2 \cdot 4H_2O$, and a mixture thereof.

The $H_2PO_4^-$ can be selected from $NH_4H_2PO_4$, $NaH_2PO_4$, or a mixture thereof.

The magnesium ion complexing agent can be ethylene diamine tetraacetic acid (EDTA) or a derivative thereof, salicylic acid or a derivative thereof, an amino acid, and a mixture thereof.

The electrochemical deposition method can be a constant potential cathodic deposition method, a galvanostatic deposition method, a unidirectional pulse electrodeposition method, or a bidirectional pulse electrodeposition method.

The magnesium alloy can be a magnesium-zinc alloy or a magnesium-aluminum alloy.

The disclosure also provides a magnesium or magnesium alloy comprising a coating prepared according to the above-mentioned method.

Advantages of the method of preparing a coating of biomedical magnesium alloys are summarized as follows:
1. The crystal of the coating comprising zinc, calcium and phosphorus belongs to monoclinic crystal, is massive and compact. The contact area of the coating with the substrate material is large and the bonding strength is high. The magnesium ion complexing agent can promote the formation of the coating.
2. Electrochemical tests show that the self-corrosion potential of the coated magnesium alloy increases and the self-corrosion current density decreases. The corrosion resistance of the magnesium alloys is improved.
3. The coating has better biodegradability and biocompatibility.

BRIEF DESCRIPTION OF THE DRAWINGS

FIG. 2B is a table showing the elemental composition of the coating in FIG. 2A;

DETAILED DESCRIPTION

Figure 1:
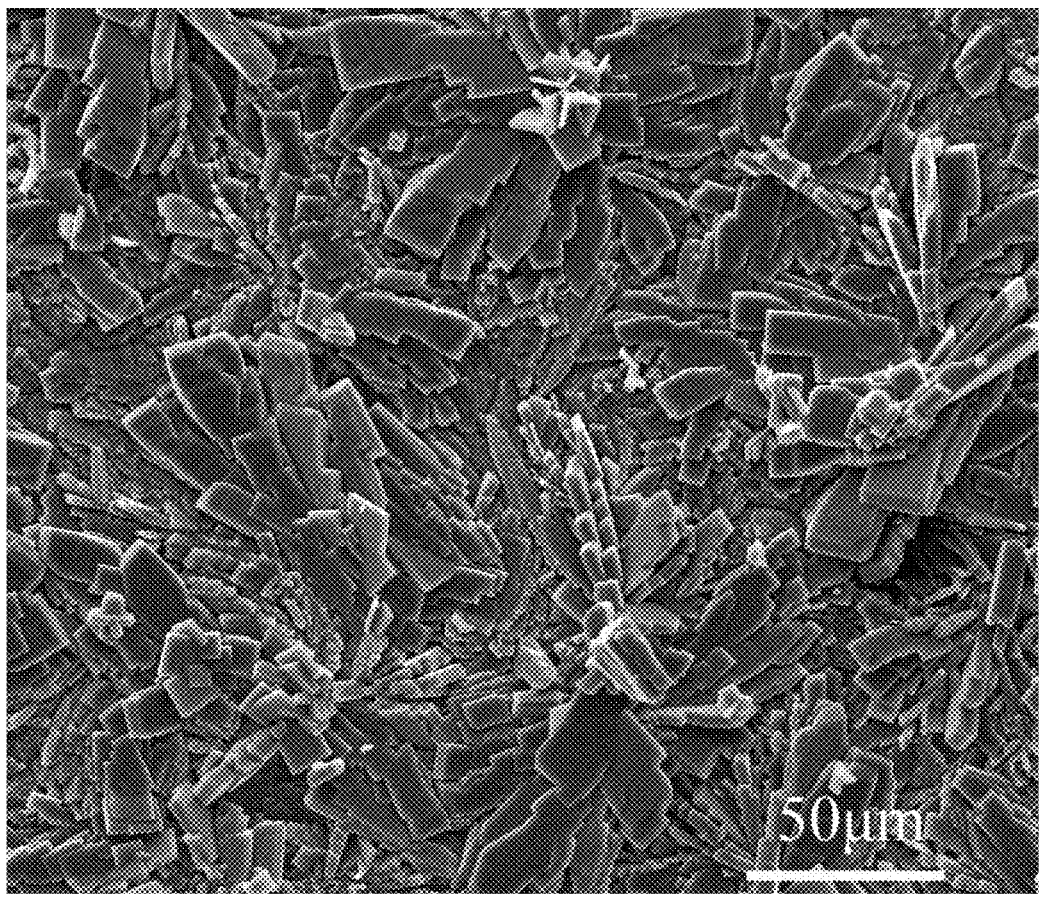
FIG. 1 is a scanning electron microscope (SEM) image of a coating in Example 1 in the disclosure.

To further illustrate, experiments detailing a method of preparing a coating of biomedical magnesium alloys are described below. It should be noted that the following examples are intended to describe and not to limit the description.

Example 1

A method of preparing a coating of biomedical magnesium and magnesium alloys for improving the corrosion resistance and biocompatibility of the biomedical magnesium and magnesium alloys is detailed as follows:

1) pretreatment of substrate material: a Mg—Zn—Ca alloy was cut into 25 mm×10 mm×4 mm rectangular blocks as a substrate material. The substrate material was mechanically polished using 100#, 200#, 400#, 600# and 800# metallographic sandpapers in sequence, then placed in an anhydrous ethanol/acetone (the volume ratio was 1:1) mixed solution for ultrasonic cleaning (40 kHz) for 10 min, and then dried in the air;

2) preparation of electrolyte: $Ca(NO_3)_2 \cdot 4H_2O$, $Zn(NO_3)_2 \cdot 6H_2O$, $NH_4H_2PO_4$ and $NaNO_3$ were dissolved in water to yield an electrolyte, the electrolyte comprised: $Ca(NO_3)_2 \cdot 4H_2O$, 40 mmol/L; $Zn(NO_3)_2 \cdot 6H_2O$, 2 mmol/L; $NH_4H_2PO_4$, 28 mmol/L; and $NaNO_3$, 0.1 mol/L;

3) the substrate material in 1) was employed as a cathode, a graphite flake as an anode, the electrolyte was heated to 80° C., and the cathode and the anode were synchronously immersed into the electrolyte in 2), the distance between the cathode and the anode was 5 cm;

4) a bidirectional pulse electrodeposition method was implemented in the electrolyte; the pulse frequency was 10 Hz, positive peak current 10 mA/cm$^2$, duty cycle 10%, reverse peak current 20 mA/cm$^2$, duty cycle 4%, deposition time 40 min; and 5) a resulting product in 4) was collected, washed using deionized water, and dried in the air, to yield a coating of biomedical magnesium and magnesium alloys that features high corrosion resistance and biocompatibility.

Figure 2A:
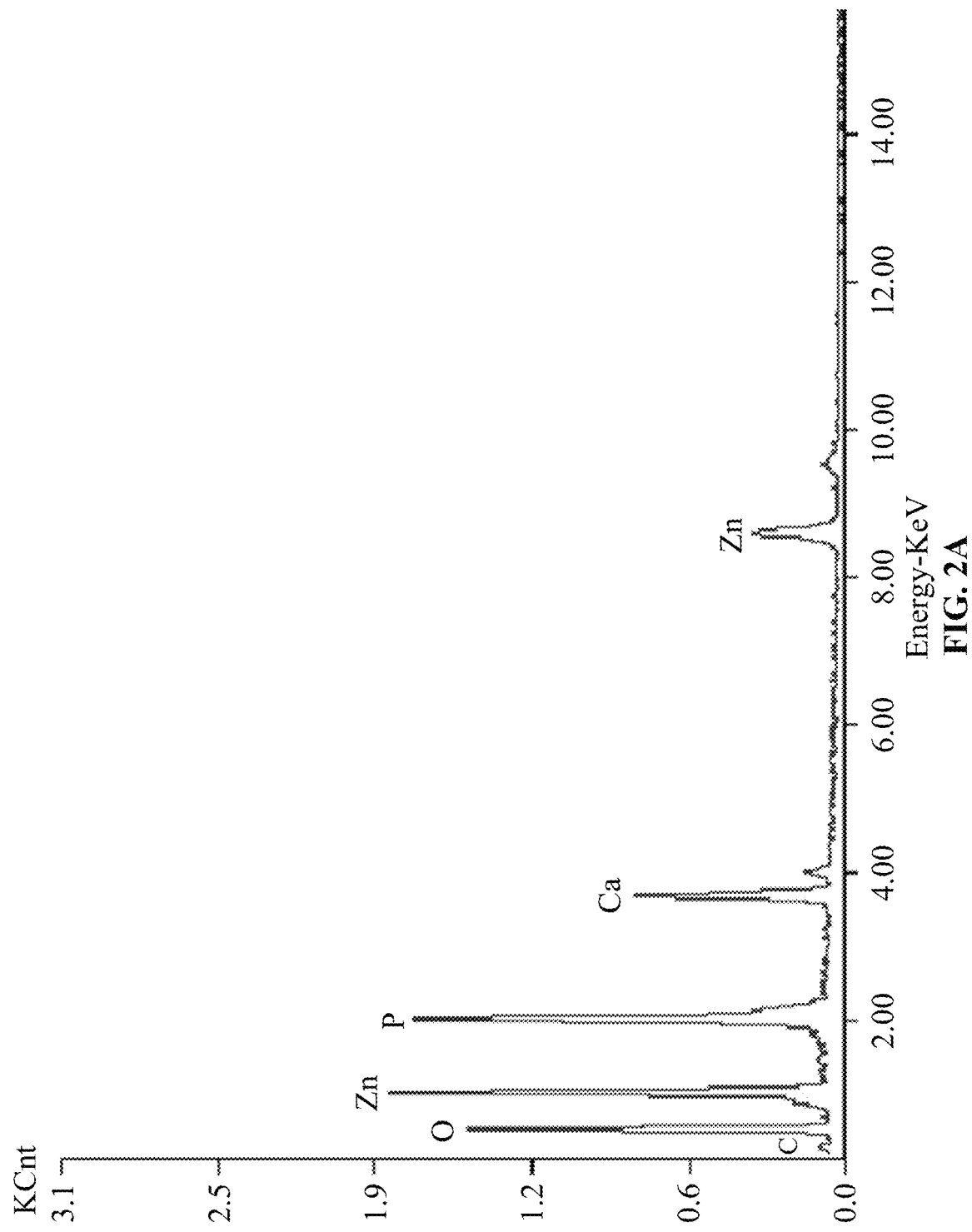
FIG. 2A is an energy dispersive spectrometer (EDS) graph of a coating in Example 1 in the disclosure.
Figure 3:
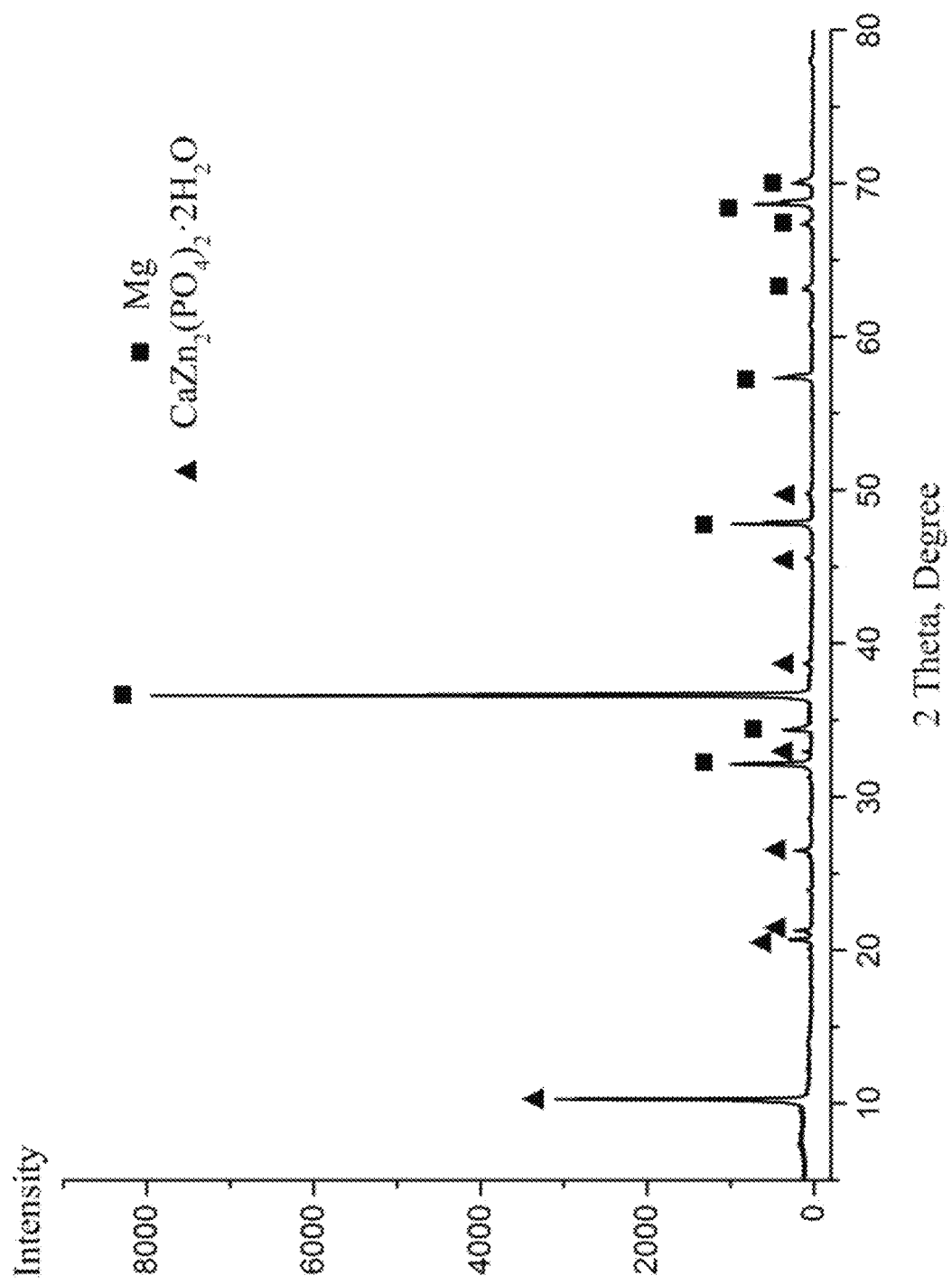
FIG. 3 is an X-ray diffraction (XRD) image of a coating in Example 1 in the disclosure.

FIG. 1 shows a scanning electron microscope (SEM) image of the resulting coating; as can be shown, the coating crystals were massive and tightly arranged on the surface of the sample. FIGS. 2A and 2B show an energy dispersive spectrometer (EDS) graph and the elemental composition of the coating; as can be shown, there was no magnesium element in the coating, indicating that the substrate material was completely covered by the coating, and the coating has a certain thickness. The coating comprises zinc (Zn), calcium (Ca), and phosphorus (P), the mole ratio of Zn to Ca is about 2:1, and (Zn+Ca)/P is 1.28. FIG. 3 is an X-ray diffraction (XRD) image of the coating, indicating that the main component of the coating is $CaZn_2(PO_4)_2 \cdot 2H_2O$, and in combination with the EDS data, the mole ratio 1.28 of the (Zn+Ca)/P is obviously less than the mole ratio 1.5 in the chemical formula, which means the coating is a non-stoichiometric coating.

The (Ca+Zn)/P mole ratio of the coating is non-stoichiometric. The non-stoichiometric coating can be degraded gradually with the time passing by in the physiological environment, which does not affect the degradation properties of the magnesium alloy as a biodegradable bone implant material, and the coating will gradually release $Zn^{2+}$ during the degradation process; the $Zn^{2+}$ can play a sustained active role in fracture healing.

Figure 4:
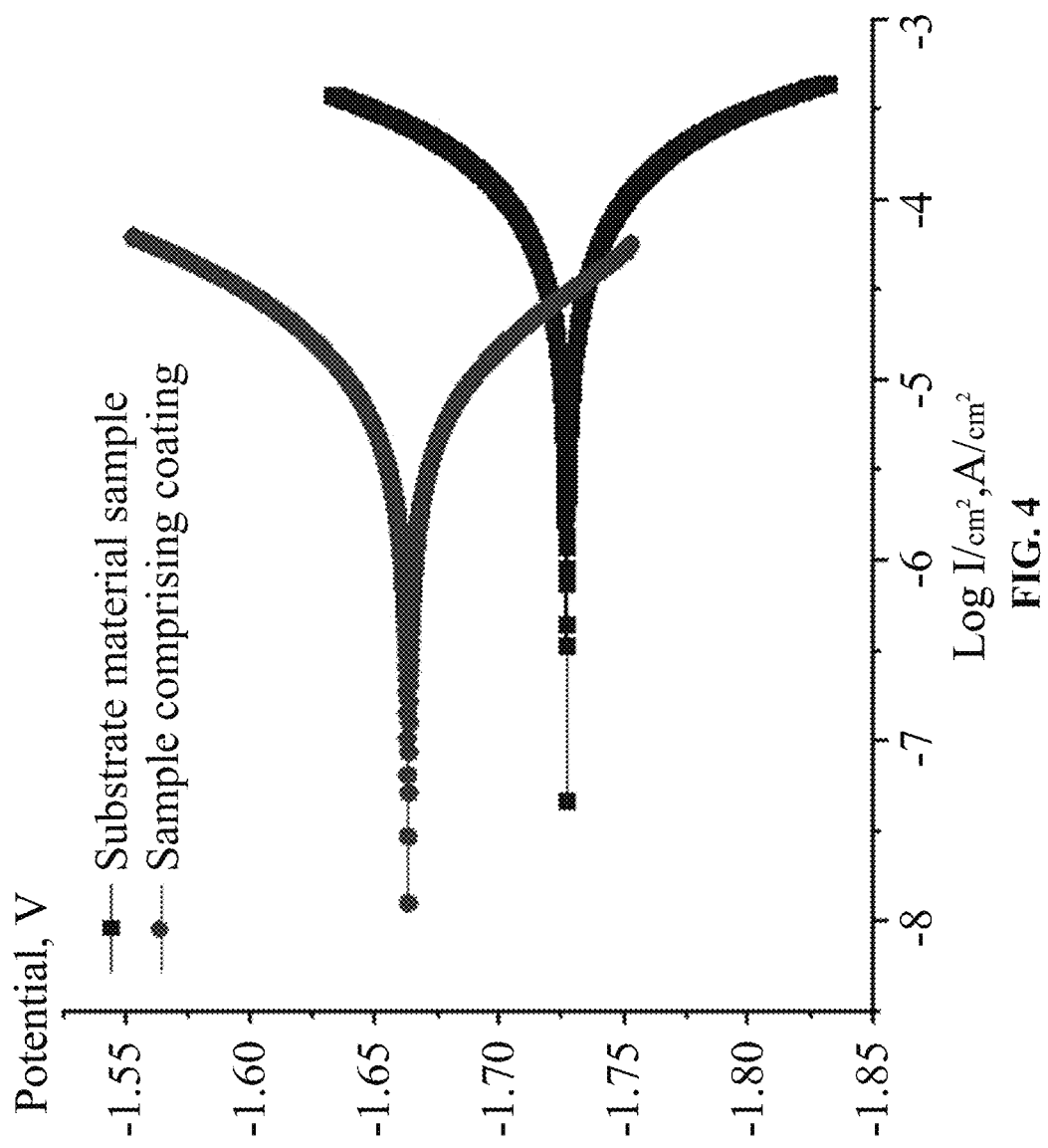
FIG. 4 shows polarization curves of a substrate material before and after being coated in Example 1 in the disclosure.

The corrosion resistance performance of the coating was tested in Kokubo's simulated body fluids (SBF) (refer to GB/T 24916-2009 standard). As shown in FIG. 4, the corrosion potential increases by 70 mV, the corrosion current density increases by two orders of magnitude, indicating that the coating can effectively reduce the corrosion rate of the substrate material.

Example 2

A method of preparing a coating of biomedical magnesium and magnesium alloys for improving the corrosion resistance and biocompatibility of the biomedical magnesium and magnesium alloys is detailed as follows:

1) pretreatment of substrate material: a Mg—Zn—Y—Nd alloy was cut into 25 mm×10 mm×4 mm rectangular blocks as a substrate material. The substrate material was mechanically polished using 100#, 200#, 400#, 600# and 800# metallographic sandpapers in sequence, then placed in an anhydrous ethanol/acetone (the volume ratio was 1:1) mixed solution for ultrasonic cleaning (40 kHz) for 10 min, and then dried in the air;

2) preparation of electrolyte: $Ca(NO_3)_2$, $Zn(H_2PO_4)_2 \cdot 2H_2O$, $NaH_2PO_4$, $NaNO_3$ and $Na_2EDTA$ were dissolved in water to yield an electrolyte, the electrolyte comprised: $Ca(NO_3)_2$, 30 mmol/L; $Zn(H_2PO_4)_2 \cdot 2H_2O$, 0.8 mmol/L; $NaH_2PO_4$, 15 mmol/L; $NaNO_3$, 0.1 mol/L; and $Na_2EDTA$, 0.005 mol/L;

3) the substrate material in 1) was employed as a cathode, a graphite flake as an anode, the electrolyte was heated to 90° C., and the cathode and the anode were synchronously immersed into the electrolyte in 2), the distance between the cathode and the anode was 3 cm;

4) a unidirectional pulse electrodeposition method was implemented in the electrolyte; the pulse frequency was 10 Hz, peak current 10 mA/cm$^2$, duty cycle 10%, and deposition time 30 min; and 5) a resulting product in 4) was collected, washed using deionized water, and dried in the air, to yield a coating of biomedical magnesium and magnesium alloys that features high corrosion resistance and biocompatibility.

Example 3

A method of preparing a coating of biomedical magnesium and magnesium alloys for improving the corrosion resistance and biocompatibility of the biomedical magnesium and magnesium alloys is detailed as follows:

1) pretreatment of substrate material: a magnesium alloy AZ31 was cut into 25 mm×10 mm×4 mm rectangular blocks as a substrate material. The substrate material was mechanically polished using 100#, 200#, 400#, 600# and 800# metallographic sandpapers in sequence, then placed in an anhydrous ethanol/acetone (the volume ratio was 1:1) mixed solution for ultrasonic cleaning (40 kHz) for 10 min, and then dried in the air;

2) preparation of electrolyte: $Ca(NO_3)_2 \cdot 4H_2O$, $Zn(NO_3)_2 \cdot 6H_2O$, $NH_4H_2PO_4$, $NaNO_3$ and Cysteine were dissolved in water to yield an electrolyte, the electrolyte comprised: $Ca(NO_3)_2 \cdot 4H_2O$, 50 mmol/L; $Zn(NO_3)_2 \cdot 6H_2O$, 8 mmol/L; $NH_4H_2PO_4$, 27 mmol/L; $NaNO_3$, 0.1 mol/L; and Cysteine, 0.05 mol/L;

3) the substrate material in 1) was employed as a cathode, a graphite flake as an anode, the electrolyte was heated to 70° C., and the cathode and the anode were synchronously immersed into the electrolyte in 2), the distance between the cathode and the anode was 4 cm;

4) a galvanostatic deposition method was implemented in the electrolyte; the current density was 0.5 mA/cm$^2$, and deposition time 60 min; and 5) a resulting product in 4) was collected, washed using deionized water, and dried in the air, to yield a coating of biomedical magnesium and magnesium alloys that features high corrosion resistance and biocompatibility.

Example 4

A method of preparing a coating of biomedical magnesium and magnesium alloys for improving the corrosion resistance and biocompatibility of the biomedical magnesium and magnesium alloys is detailed as follows:

1) pretreatment of substrate material: a pure magnesium was cut into 25 mm×10 mm×4 mm rectangular blocks as a substrate material. The substrate material was mechanically polished using 100#, 200#, 400#, 600# and 800# metallographic sandpapers in sequence, then placed in an anhydrous ethanol/acetone (the volume ratio was 1:1) mixed solution for ultrasonic cleaning (40 kHz) for 10 min, and then dried in the air;

2) preparation of electrolyte: $Ca(NO_3)_2 \cdot 4H_2O$, $Zn(NO_3)_2 \cdot 6H_2O$, $NH_4H_2PO_4$, $NaNO_3$ and salicylic acid were dissolved in water to yield an electrolyte, the electrolyte comprised: $Ca(NO_3)_2 \cdot 4H_2O$, 34 mmol/L; $Zn(NO_3)_2 \cdot 6H_2O$, 1 mmol/L; $NH_4H_2PO_4$, 35 mmol/L; $NaNO_3$, 0.1 mol/L; and salicylic acid, 0.01 mol/L;

3) the substrate material in 1) was employed as a cathode, a graphite flake as an anode, the electrolyte was heated to 60° C., and the cathode and the anode were synchronously immersed into the electrolyte in 2), the distance between the cathode and the anode was 4.5 cm;

4) a galvanostatic deposition method was implemented in the electrolyte; the voltage was −3 V, and deposition time 45 min; and 5) a resulting product in 4) was collected, washed using deionized water, and dried in the air, to yield a coating of biomedical magnesium and magnesium alloys that features high corrosion resistance and biocompatibility.

Unless otherwise indicated, the numerical ranges involved include the beginning and end values. It will be obvious to those skilled in the art that changes and modifications may be made, and therefore, the aim in the appended claims is to cover all such changes and modifications.

What is claimed is:

1. A method, comprising:
   1) employing pure magnesium or a magnesium alloy as a substrate material, and sanding and cleaning the substrate material;
   2) preparing an electrolyte comprising 0.8-8 mmol/L of $Zn^{2+}$, 30-50 mmol/L of $Ca^{2+}$, 15-35 mmol/L of $H_2PO_4^-$, 0-0.5 mol/L of $NaNO_3$, and 0-0.05 mmol/L of a magnesium ion complexing agent;
   3) employing the substrate material in 1) as a cathode, a graphite flake as an anode, heating the electrolyte to a temperature of between 60 and 90° C., and synchronously immersing the cathode and the anode into the electrolyte in 2), a distance between the cathode and the anode being between 3 and 5 cm; and
   4) implementing an electrochemical deposition method in the electrolyte for between 20 and 60 min.

2. The method of claim 1, wherein the $Zn^{2+}$ is selected from $Zn(NO_3)_2 \cdot 6H_2O$, $Zn(H_2PO_4)_2 \cdot 2H_2O$, and a mixture thereof.

3. The method of claim 1, wherein the $Ca^{2+}$ is selected from $Ca(NO_3)_2$, $Ca(NO_3)_2 \cdot 4H_2O$, and a mixture thereof.

4. The method of claim 1, wherein the $H_2PO_4^-$ is selected from $NH_4H_2PO_4$, $NaH_2PO_4$, and a mixture thereof.

5. The method of claim 1, wherein the magnesium ion complexing agent is ethylene diamine tetraacetic acid (EDTA) or a derivative thereof, salicylic acid or a derivative thereof, an amino acid, or a mixture thereof.

6. The method of claim 1, wherein the electrochemical deposition method is a constant potential cathodic deposition method, a galvanostatic deposition method, a unidirectional pulse electrodeposition method, or a bidirectional pulse electrodeposition method.

7. The method of claim 1, wherein the magnesium alloy is a magnesium-zinc alloy or a magnesium-aluminum alloy.

* * * * *